United States Patent
Sun et al.

(10) Patent No.: US 12,384,806 B2
(45) Date of Patent: Aug. 12, 2025

(54) ISOPAUCIFLORAL F PHOSPHATE COMPOUND AND PHARMACEUTICAL USE THEREOF

(71) Applicant: FUDAN UNIVERSITY, Shanghai (CN)

(72) Inventors: Xun Sun, Shanghai (CN); Meilin Tang, Shanghai (CN); Zhe Jiang, Shanghai (CN); Xiaodong Hao, Shanghai (CN); Chen Zhong, Shanghai (CN); Jun Zhu, Shanghai (CN); Nan Wang, Shanghai (CN)

(73) Assignee: FUDAN UNIVERSITY, Shanghai (CN)

( * ) Notice: Subject to any disclaimer, the term of this patent is extended or adjusted under 35 U.S.C. 154(b) by 561 days.

(21) Appl. No.: 17/908,686

(22) PCT Filed: Mar. 18, 2021

(86) PCT No.: PCT/CN2021/081571
§ 371 (c)(1),
(2) Date: Sep. 1, 2022

(87) PCT Pub. No.: WO2021/175335
PCT Pub. Date: Sep. 10, 2021

(65) Prior Publication Data
US 2023/0159572 A1    May 25, 2023

(30) Foreign Application Priority Data

Mar. 2, 2020   (CN) .......................... 202010135398.5

(51) Int. Cl.
*C07F 9/09* (2006.01)
(52) U.S. Cl.
CPC ................... *C07F 9/095* (2013.01)
(58) Field of Classification Search
CPC . C07F 9/095; C07F 9/12; A61K 31/05; A61K 31/21; A61K 31/661; A61K 31/6615; A61P 19/10; C07C 35/23; C07C 39/10
See application file for complete search history.

(56) References Cited

FOREIGN PATENT DOCUMENTS

| | | |
|---|---|---|
| CN | 105078944 | 11/2015 |
| CN | 107382909 | 11/2017 |
| WO | 2008/043567 | 4/2008 |

OTHER PUBLICATIONS

Hao, X. et al., "Synthesis, estrogenic activity, and anti-osteoporosis effects in ovariectomized rats of resveratrol oligomer derivatives" Jul. 26, 2015, European Journal of Medicinal Chemistry, vol. 102, pp. 26-38 (13 pages).
Snyder, S. et al., "Total Synthesis of Resveratrol-Based Natural Products: A Chemoselective Solution" Dec. 31, 2007, Angew. Chem. Int. Ed., vol. 46, No. 43, pp. 8186-8191 (6 pages).
Tang, M. et al., "Sulfoxide-Based Enantioselective Nazarov Cyclization: Divergent Syntheses of (+)-Isopaucifloral F, (+)-Quadrangularin A, and (+)-Pallidol" Aug. 30, 2016, Chemistry, vol. 22, No. 41, pp. 14535-14539 (5 pages).
International Search Report for PCT/CN2021/081571, dated Jun. 17, 2021 (8 pages).
Written Opinion of the ISA for PCT/CN2021/081571, dated Jun. 17, 2021 (4 pages).

*Primary Examiner* — Umamaheswari Ramachandran
(74) *Attorney, Agent, or Firm* — NIXON & VANDERHYE, PC

(57) ABSTRACT

The present invention pertains to the technical field of biomedicine, and relates to isopaucifloral F phosphate compounds and pharmaceutical uses thereof. It has been confirmed through experiments that said isopaucifloral F phosphate compounds and pharmaceutically acceptable salts thereof have effects on the bone remodeling process by exerting their anti-osteoporosis efficacy through a dual-mode mechanism of action of promoting osteogenesis and reducing osteoclast resorption, have the characteristics of high bioavailability, stable metabolism and good safety, and can be used to prepare a new generation of anti-osteoporosis drugs.

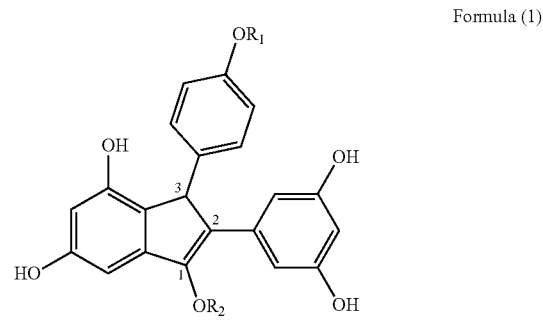

Formula (1)

8 Claims, 3 Drawing Sheets

ISOPAUCIFLORAL F PHOSPHATE COMPOUND AND PHARMACEUTICAL USE THEREOF

This application is the U.S. national phase of International Application No. PCT/CN2021/081571 filed Mar. 18, 2021 which designated the U.S. and claims priority to CN 202010135398.5 filed Mar. 2, 2020, the entire contents of each of which are hereby incorporated by reference.

TECHNICAL FIELD

The present invention pertains to the technical field of biomedicine, and relates to isopaucifloral F phosphate compounds and pharmaceutical uses thereof, in particular to phosphate-modified compounds of natural isopaucifloral F molecules and their uses in the preparation of anti-osteoporosis medicaments.

BACKGROUND

The prior art discloses that osteoporosis (OP) is a systemic skeletal metabolic disease with multiple etiologies to which the elderly and postmenopausal women are prone; which is characterized by the decreased bone strength, increased bone fragility, and an increased risk of fractures due to decreased bone mass and degenerated bone tissue microstructures, and of which the clinical symptoms are mostly bone pain and fractures. Clinical practice shows that fractures most often occur in such parts as the hip, wrist and spine, with a mortality rate of 20%-24% within one year after hip fractures, and thus would seriously affect the quality of life of patients, and even be life-threatening. According to statistics, the global incidence of osteoporosis has exceeded 25%, and its incidence has jumped to the seventh place among the common and frequently-occurring diseases. The World Health Organization (WHO) considers osteoporosis as the second most important health problem after coronary heart disease, as it can occur in any racial or ethnic group at any age and has been affecting millions of people around the world, especially when both human health and economic development are facing severe challenges with increased aging of the global population. Therefore, how to treat osteoporosis has become a research hotspot in modern medicine.

In clinical practice, drugs for treatment of osteoporosis are divided into three categories according to their mechanism of action on the bone remodeling process:

(1) Bone resorption inhibiting drugs comprising the following four types:
① Alendronate sodium diphosphate which inhibits a key enzyme pyrophosphate synthase in osteoclasts, inhibits the activity of osteoclasts and thus inhibits osteoclast-mediated bone resorption. However, this type of drug strongly inhibits bone resorption and has a long half-life, and thus long-term use thereof would cause potential skeletal toxicity (i.e., osteonecrosis of the jaw and atypical femoral fractures) and nephrotoxicity, and meanwhile the clinical applications would also be greatly reduced due to gastrointestinal intolerance of patients to bisphosphonates;

② Estrogen supplement therapies for alleviating osteoporosis in postmenopausal women. Long-term use of estrogen will lead to an increased risk of having breast cancer, so estrogen supplements have not been used as routine therapeutic drugs in clinical practice;

③ Selective estrogen receptor modulators represented by Raloxifene. Raloxifene exhibits agonistic activities in bones and can increase bone mineral densities. The important defect of Raloxifene lies in its absolute bioavailability of only 2%; and ④ Calcitonin represented by Denosumab which is a human full-length monoclonal antibody targeting and binding to a nuclear factor-KO receptor activator ligand (RANKL), thereby inhibiting the generation of osteoclasts and inhibiting bone resorption; however, due to the widespread presence of RANKL in most tissues and immune systems, long-term use of Denosumab mainly has a variety of toxic side effects.

(2) Osteogenesis promoting drugs: a synthetic parathyroid hormone-related peptide, Teriparatide, is the only effective osteogenesis stimulator currently recommended in clinical practice, but Teriparatide is expensive and needs to be administrated daily via subcutaneous injection, which severely limits its clinical use, and is now used as a second-line drug for the treatment of osteoporosis.

(3) Dual-mode drugs for promoting osteogenesis while inhibiting bone resorption: Strontium Ranelate (SR) is currently the only dual-mode drug that can reduce bone resorption and promote osteogenesis at the same time; by stimulating the formation of new bone tissues while reducing bone resorption, this drug can reduce the incidence of systematic bone fractures, and has significant therapeutic effects, but it has been reported that Strontium Ranelate can increase the incidence of non-fatal myocardial infarction, which forces regulatory agencies to reconsider its efficacy and risk, and its safety needs to be further improved.

The efficacy and safety of long-term use of drugs are the main problems that need to be solved in the current clinical research on anti-osteoporosis drugs. Therefore, it is of great significance to research dual-mode anti-osteoporosis drugs with high efficacy and low toxicity for reducing bone resorption while promoting osteogenesis.

In early stages, the research team of the present application isolated from a kidney-tonifying medicinal plant gorse root a variety of natural polyhydroxy phenolic resveratrol dimers with structural characteristics and better activities than resveratrol, as selective estrogen receptor modulators, and they exhibit estrogen-like effects on bone, increase bone densities, and have no adverse reactions. At the same time, the research team constructed a sample library of four types of natural dominant skeleton resveratrol dimer compounds with a total of 500 compounds, and conducted the systematic lead compound discovery and druggability research on hit compounds with drug-like dominant skeletons. Experiments showed that the natural product isopaucifloral F can be used as a selective agonist of estrogen receptor ERβ, but it has a defect of having no significant anti-osteoporosis efficacy.

Based on the foundation and current state of the prior art, the present invention intends to provide the use of an isopaucifloral F phosphate compound for the preparation of anti-osteoporosis medicaments. Such compounds have high safety, good metabolic stability and high bioavailability, and exert anti-osteoporosis efficacy through a dual-mode mecha-

SUMMARY OF THE INVENTION

An object of the present invention is to provide isopaucifloral F phosphate compounds and their uses for the preparation of anti-osteoporosis medicaments based on the foundation and current state of the prior art.

The present invention found through experiments based on the prior art that the natural product isopaucifloral F can be used as a selective agonist of estrogen receptor ERβ, but it has a defect of having no significant anti-osteoporosis efficacy; the main reason is that its molecular structure contains multiple phenolic hydroxyl groups which would easily bind to glucuronic acid in the body and be excreted from the body.

The present invention optimizes the molecular structure of isopaucifloral F to improve the metabolic properties and bioavailability of lead substances by introducing the predominant phosphate group present in the molecular structure of the anti-osteoporosis drug Alendronate into sites of Isopaucifloral F which are prone to metabolization, so as to design and prepare new metabolically stable phosphate target compounds under the drug design concept of pharmacophore grafting. The prepared compounds have been proved through experiments to have high safety, good metabolic stability, and high bioavailability, and exert anti-osteoporosis efficacy through a dual-mode mechanism of action of reducing osteoclast resorption and promoting osteogenesis.

Specifically, the present invention provides isopaucifloral F phosphate compounds of the following formula (1) and pharmaceutically acceptable salts thereof.

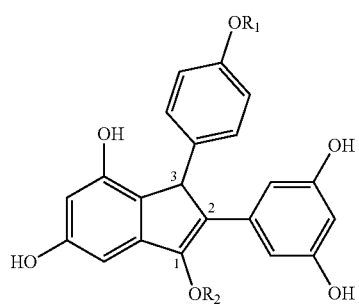
(1)

wherein $R_1$ is independently a phosphate group or a hydrogen atom, and $R_2$ is independently a phosphate group;

when $R_1$ is a hydrogen atom, $R_2$ is independently a phosphate group

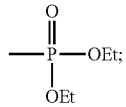

when $R_1$ is a phosphate group

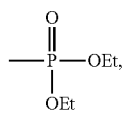

$R_1=R_2$.

The present invention provides a method for synthesizing the above isopaucifloral F phosphate medicaments. The present invention adopts the early-stage synthesis method: using 3,5-dimethoxybenzoic acid (2) as the starting material, synthesizing the key intermediates 6a and 6b through the metal coupling reaction, Wittig reaction and Nazarov cyclization, and then introducing diethyl phosphate groups into the molecular structures of the key intermediates 6a and 6b through nucleophilic substitution reactions under a NaH/THF system, and finally performing demethylation on molecules in a $BBr_3/CH_2Cl_2$ system to obtain target products 1a and 1b.

The specific synthetic route is as shown in the general reaction formula (1):

Scheme 1 general reaction formula (1)

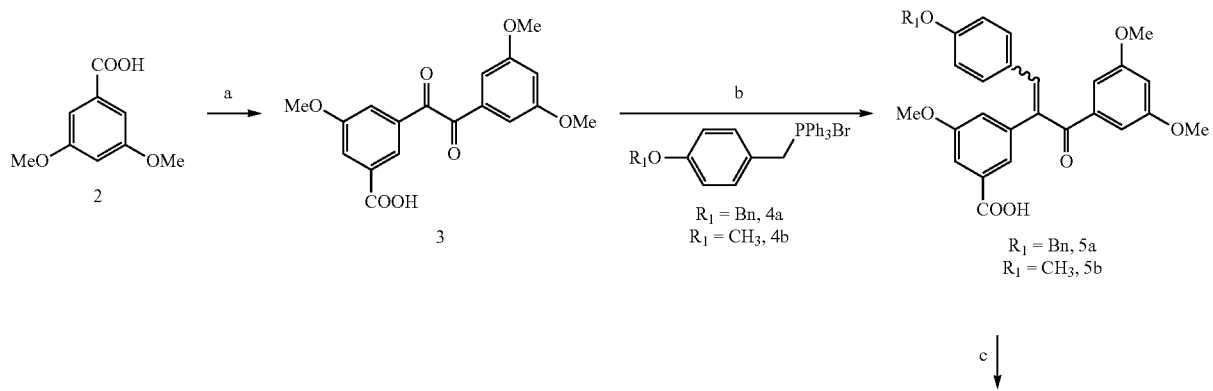

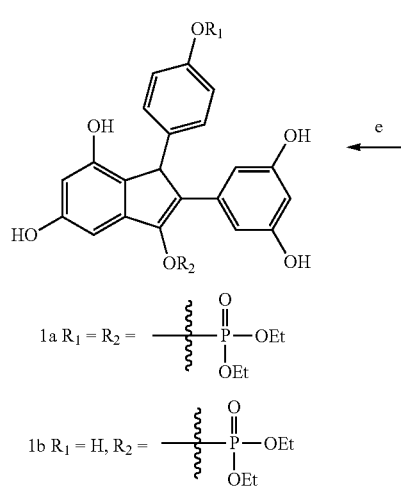
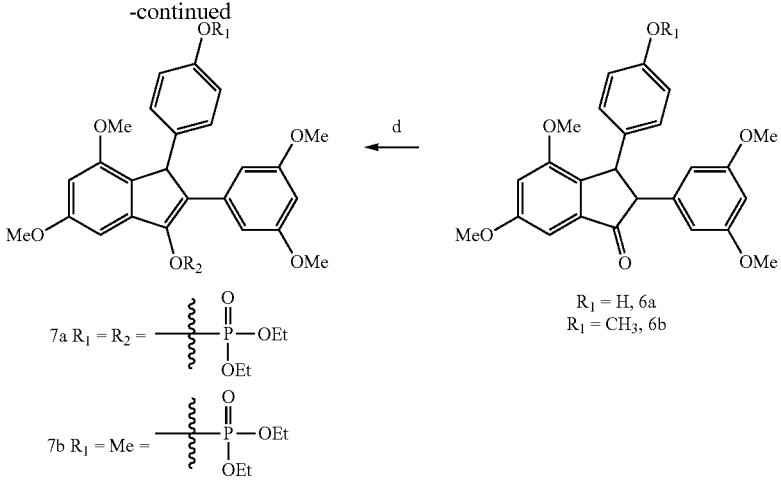

Preferably, the base used in the Wittig reaction condition (b) in the above preparation method is NaHMDS, KHMDS, LiHMDS, LDA, NaH, tBuONa, tBuOK, or n-BuLi.

Preferably, the Lewis acid used in the Nazarov cyclization condition (c) in the above preparation method is $AlCl_3$, $BF_3$, $TiCl_4$, $SnCl_4$, $Bi(OTf)_3$, or $ZnCl_2$.

Preferably, the base used in the phosphate group introduction reaction system (d) in the above preparation method is NaH, KHMDS, NaHMDS, LiHMDS, t-BuOK, or t-BuONa.

Preferably, the reagent used in the molecule demethylation reaction system (e) in the above preparation method is $BBr_3$ or $AlCl_3$.

In the above reactions, the ratio of isopaucifloral F to phosphate group fragments is preferably 1:2.5 (reaction step e).

Experiments have been carried out in the present invention, and show that the present compounds have pharmacological research value and can treat osteoporosis. Such compounds have good metabolic stability, high bioavailability, and high safety, and exert anti-osteoporosis efficacy through a dual-mode mechanism of action of promoting osteogenesis and inhibiting osteoclast resorption.

The examples of the present invention provide data about lipid-water partition coefficients, plasma stability test, the mechanism of action of promoting osteogenesis and inhibiting osteoclast resorption of 1a and 1b; and data about metabolic stability in human liver microsomes, in vivo pharmacokinetics in rats, acute toxicity, and pharmacodynamics of a zebrafish osteoporosis model.

The present invention also provides uses of the isopaucifloral F phosphate compounds and pharmaceutically acceptable salts thereof for the preparation of anti-osteoporosis medicaments, and further prepares a pharmaceutical composition for treating osteoporosis which comprises said isopaucifloral F phosphate compounds and pharmaceutically acceptable salts and pharmaceutically acceptable excipients thereof.

The present isopaucifloral F phosphate racemate mixtures or optically pure isomers and pharmaceutically acceptable salts thereof can be prepared into various formulations comprising a safe and effective amount of an isopaucifloral F phosphate racemate mixture, optically pure isomers or pharmaceutically acceptable salts thereof, and pharmaceutical carriers.

In the present invention, "a safe and effective amount" refers to an amount of a compound which is sufficient to significantly improve the disease without causing serious side effects. The safe and effective amount is determined according to the age, disease condition, course of treatment, etc. of the subject to be treated.

In the present invention, "pharmaceutical carriers" refer to one or more compatible solid or liquid fillers or gel substances which are suitable for human use and must have sufficient purity and low enough toxicity.

In the present invention, "compatibility" means that each component in the composition can be blended with the compounds of the present invention and with each other without significantly reducing the efficacy of the compounds.

In the present invention, some examples of pharmaceutically acceptable carriers include sugar (e.g., glucose, sucrose, lactose, etc.), starch (e.g., corn starch, potato starch, etc.), cellulose and derivatives thereof (e.g., sodium carboxymethylcellulose, sodium ethylcellulose, cellulose acetate, etc.), gelatin, talc, solid lubricants (e.g., stearic acid, magnesium stearate), calcium sulfate, vegetable oils (e.g., soybean oil, sesame oil, peanut oil, olive oil, etc.), polyols (e.g., propylene glycol, glycerol, mannitol, sorbitol, etc.), emulsifiers (e.g., Tween®), wetting agents (e.g., sodium dodecyl sulfate), colorants, flavors, stabilizers, antioxidants, preservatives, pyrogen-free water, etc.

The present invention has the following beneficial effects compared with the prior art: at present, the most effective anti-osteoporosis drugs in clinical practice are dual-mode drugs for promoting osteogenesis while inhibiting bone resorption. The only representative drug Strontium Ranelate causes a risk of increasing the incidence of non-fatal myocardial infarction, and its safety needs to be further improved. The isopaucifloral F phosphate compounds of the present invention and salts thereof have high safety and exert anti-osteoporosis effects through the dual mechanisms of promoting osteogenesis and inhibiting bone resorption. Such compounds have good metabolic stability and high bioavailability, and are expected to meet urgent clinical needs.

DETAILED DESCRIPTION OF THE INVENTION

Figure 1:
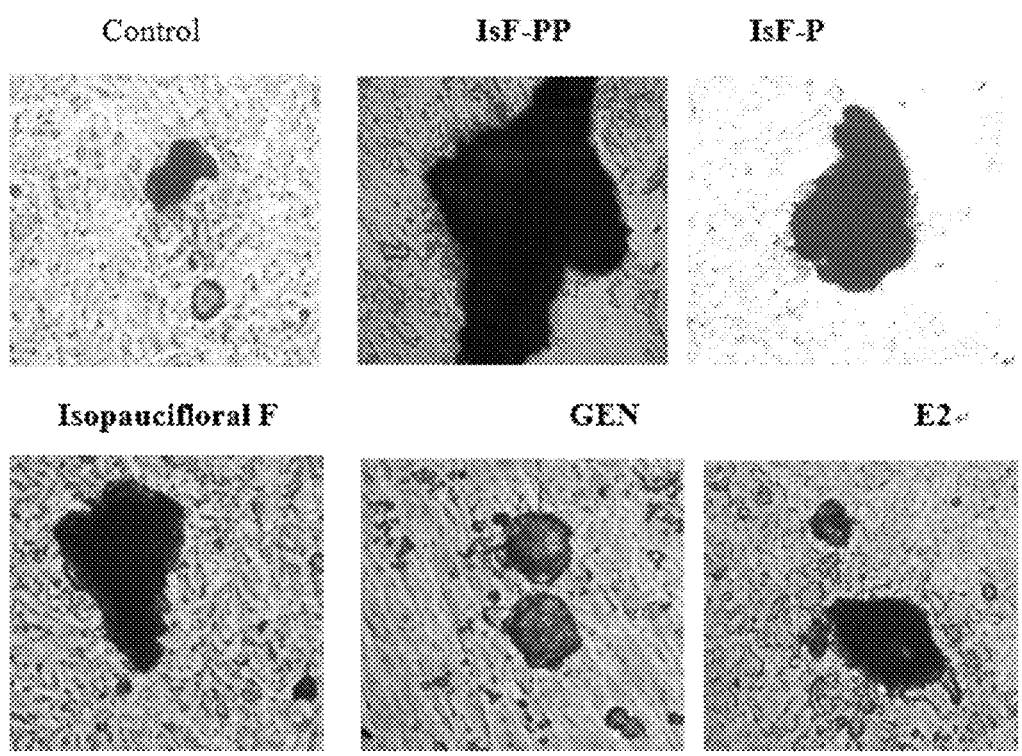
FIG. 1 shows the single crystal formed by Alizarin Red and calcium nodules as observed under a 40× inverted microscope.

The present invention will be further described below in conjunction with the examples, but the present invention is in no way limited by these examples.

Example 1: Synthesis of 3,3',5,5'-tetramethoxydiphenylethanedione (3)

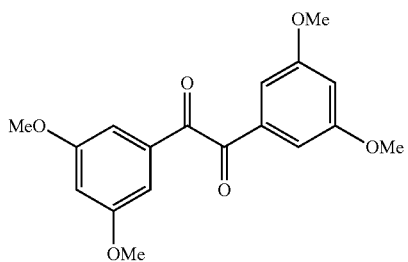

23.34 g (0.18 mol) of naphthalene and 1.26 g of small shards of a metallic lithium ribbon were sequentially added into a 250 mL three-necked flask. The metallic lithium ribbon should be quickly cut to reduce its contact with the air, as the metal lithium has active chemical properties and will easily have oxides generated on its surface in the air. Under nitrogen protection, 150 mL of anhydrous THF was added to fully dissolve naphthalene. After vigorous stirring for 1 to 3 minutes, the reaction solution changed from colorless to green to black. After stirring at room temperature for 6 to 8 hours, a lithium naphthalene (LiN) reagent was prepared for use. Additionally, 15.00 g (82.35 mmol) of 3,5-dimethoxybenzoic acid 34 was weighed and placed in a 500 mL three-necked flask under nitrogen protection. 300 mL of anhydrous THF was added to fully dissolve 3,5-dimethoxybenzoic acid. Under the condition of ice bath, the LiN reagent prepared in advance was sucked out with a syringe and added to the THF solution system with 3,5-dimethoxybenzoic acid dissolved therein. The reaction solution turned from yellow to dark brown. Water was added to terminate the reaction. THF was spun off, extraction was carried out three times with a solvent $CH_2Cl_2$, a dichloromethane layer was rinsed with a saturated NaCl solution, dried over anhydrous $Na_2SO_4$, and concentrated to obtain a yellow crude product. The yellow crude product was firstly subjected to preliminary separation by a normal phase column, and after the unreacted naphthalene in the system was washed away with n-hexane, the remaining yellow solid was recovered with dichloromethane as a solvent. After being spin-dried, it was recrystallized with a system of petroleum ether:ethyl acetate=2:1 to obtain a yellow-green solid powder, namely a pure product of 3,3',5,5'-tetramethoxydiphenylethanedione (3) with a yield of 47.6%. $^1$H-NMR (CDCl$_3$, 400 MHz) δ ppm: 3.83 (s, 12H), 6.74 (s, 2H), 7.07 (d, J=1.7 Hz, 4H).

Example 2: Synthesis of 1,2-bis-(3,5-dimethoxyphenyl)-3-(4-methoxyphenyl)-2-propen-1-one (5a)

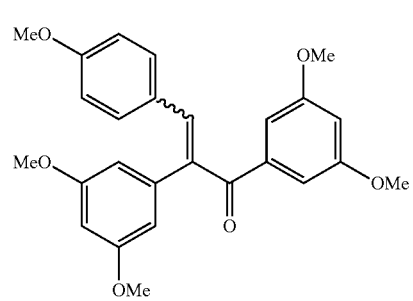

500 mg (1.51 mmol) of 3,3',5,5'-tetramethoxydiphenylethanedione (3) and 700 mg (1.67 mmol) of (4-methoxybenzyl)triphenyl phosphonium chloride salt (4a) were sequentially added into a 50 mL two-necked flask under nitrogen protection, dissolved with addition of 20 mL of anhydrous toluene, and 1.67 mL (1.0 M, 1.67 mmol) of a KHMDS solution in THF was added dropwise at a uniform rate. When TLC showed the complete reaction of ethanedione (3), water could be added to quench the reaction. Ethyl acetate extraction was performed, an organic layer was dehydrated with a saturated NaCl solution, dried over anhydrous $Na_2SO_4$, concentrated and purified by silica gel column chromatography (n-hexane:acetone=10:1) to obtain a yellow oil 5a with a yield of 94.4%. $^1$H-NMR (CDCl$_3$, 400 MHz) δ ppm: 3.72-3.77 (m, 15H), 6.38-6.39 (m, 1H), 6.56-6.59 (m, 3H), 6.72-6.75 (m, 2H), 7.09-7.23 (m, 5H).

Example 3: Synthesis of 4,6-dimethoxy-3-(4-hydroxyphenyl)-2-(3,5-dimethoxyphenyl)-2,3-dihydroindan-1-one (6a)

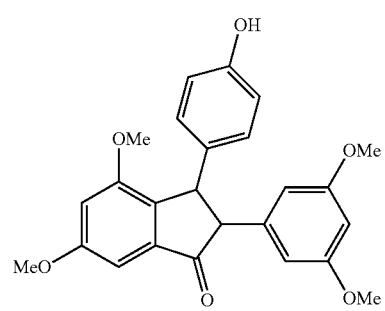

510.2 mg (1.11 mmol) of compound 5a was weighed and placed into a 100 mL single-necked flask and fully dissolved with anhydrous toluene. Afterwards, 149 mg (1.2 mmol) of solid AlCl$_3$ was slowly added under stirring, the reaction system would gradually turn orange red, let it stand at room temperature overnight, it was monitored by TLC until the reaction was complete and the product spot was single. A small amount of water was added to the reaction system to terminate the reaction. After ethyl acetate (EA) extraction, drying over anhydrous $Na_2SO_4$, and concentration and purification by silica gel column chromatography (n-hexane:acetone=8:1), a foamy yellow solid 6a was obtained with a yield of 89.6%. $^1$H NMR (400 MHz, CDCl$_3$) δ ppm: 6.96

(1H, s), 6.72 (1H, s), 6.44 (4H, s), 6.17 (1H, s), 5.91 (2H, d, J=2.30 Hz), 4.90 (1H, d, J=2.75 Hz), 4.26 (1H, d, J=2.75 Hz), 3.88 (3H, s), 3.70 (3H, s), 3.57 (6H, s). ESI-MS m/z: 421.2 [M+H]$^+$; C$_{25}$H$_{24}$O$_6$: HRMS calcd. 421.1682 [M+H]$^+$, found 421.1335.

Example 4: Synthesis of 4,6-dimethoxy-3-(4-methoxyphenyl)-2-(3,5-dimethoxyphenyl)-2,3-dihydroindan-1-one (6b)

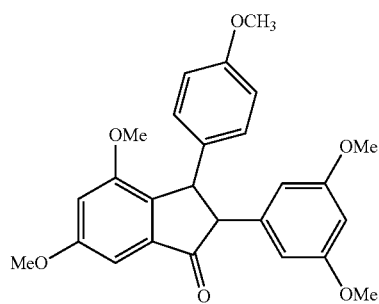

6b 1.24 g (2.85 mmol) of compound 5b was weighed into a 100 mL single-necked flask, and fully dissolved with addition of 40 mL of dichloromethane. 3.8 mL (14.26 mmol) of BF$_3$·Et$_2$O was slowly added dropwise at room temperature and stirred overnight, TLC showed that the starting material substantially disappeared and the product spot was single, and a small amount of water was added to terminate the reaction. After extraction with CH$_2$Cl$_2$, washing with a saturated NaHCO$_3$ aqueous solution, washing with water until neutral, dehydration with a saturated NaCl solution, drying over anhydrous Na$_2$SO$_4$, and solvent concentration, a crude product was obtained as a yellow-white solid. It was subjected to normal phase column separation, with petroleum ether:acetone=8:1. The product 6b was a white solid with a yield of 94.4%. $^1$H NMR (400 MHz, CDCl$_3$) δ ppm: 6.96-6.23 (m, 9H), 4.52 (1H, d, J=2.60 Hz), 3.87 (3H, s), 3.78 (3H, s), 3.73 (6H, s). ESI-MS m/z: 435.2 [M+H]$^+$; C$_{26}$H$_{26}$O$_6$: HRMS calcd. 435.1721 [M+H]$^+$, found 435.1713.

Example 5: Synthesis of Compound 7a

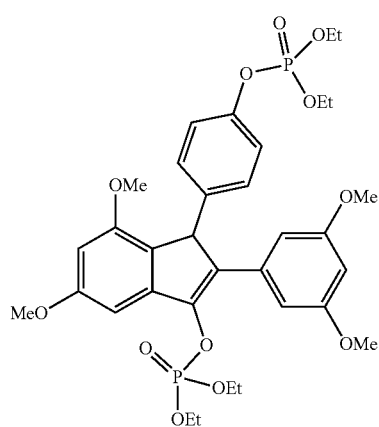

7a

A 25 mL two-necked flask was dried and cooled, and 200 mg (0.48 mmol) of compound 6a and 48 mg (1.19 mmol) of sodium hydrogen were weighed and placed in the two-necked flask under nitrogen protection. Since the reaction system had strict requirements on anhydrous conditions, anhydrous THF needed to be dried with NaH before use and then was added to the flask. Under rapid stirring, diethyl chlorophosphate (1.90 mmol) was added and refluxed overnight, and the reaction system changed from light yellow to light pink. The reaction was monitored by TLC, and the reaction of compound 6a was found to be incomplete. However, the yield could not be improved by prolonging the reaction time or supplementing diethyl chlorophosphate, so the reaction was terminated. The inorganic salt precipitate was removed by filtration, rinsing was performed with a small amount of ethyl acetate, the reaction solution was spin-dried and passed through a normal phase column for separation to obtain compound 7a as a colorless oil with a yield of 21.5%. $^1$H-NMR (400 MHz, CDCl$_3$) δ ppm: 7.09 (2H, d, J=8.0 Hz), 6.98 (2H, d, J=8.0 Hz), 6.91 (1H, d, J=2.0 Hz), 6.69 (2H, d, J=2.0 Hz), 6.28 (1H, d, J=2.0 Hz), 6.26 (1H, t, J=2.0 Hz, J=2.0 Hz), 4.86 (1H, s), 4.16-4.05 (8H, m), 3.83 (3H, s), 3.70 (6H, s), 3.59 (3H, s), 1.29-1.20 (12H, m).

Example 6: Synthesis of Compound 7b

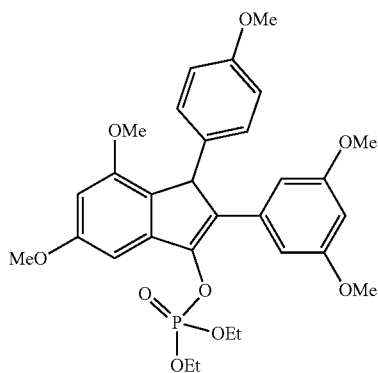

7b

A 25 mL two-necked flask was dried and cooled, 127 mg (0.29 mmol) of compound 6b and 24 mg (0.58 mmol) of sodium hydrogen were weighed and placed in the two-necked flask under nitrogen protection, and dissolved with anhydrous THF. Diethyl chlorophosphate (0.44 mmol) was added under rapid stirring, the reaction system was refluxed overnight, and the solution changed from light yellow to pink. The reaction was monitored by TLC and a pure compound 7b was isolated as a colorless oil with a yield of 76.0%. $^1$H-NMR (400 MHz, CDCl$_3$) δ ppm: 7.05 (2H, d, J=8.0 Hz), 6.92 (1H, d, J=2.0 Hz), 6.73 (2H, d, J=2.0 Hz), 6.68 (2H, d, J=8.0 Hz), 6.29 (1H, d, J=2.0 Hz), 6.27 (1H, t, J=2.0 Hz), 4.85 (1H, d), 4.25-4.04 (4H, m), 3.85 (3H, s), 3.71 (6H, s), 3.71 (3H, s), 3.61 (3H, s), 1.37-1.21 (6H, m).

Example 7: Synthesis of Target Compounds 1a and 1b

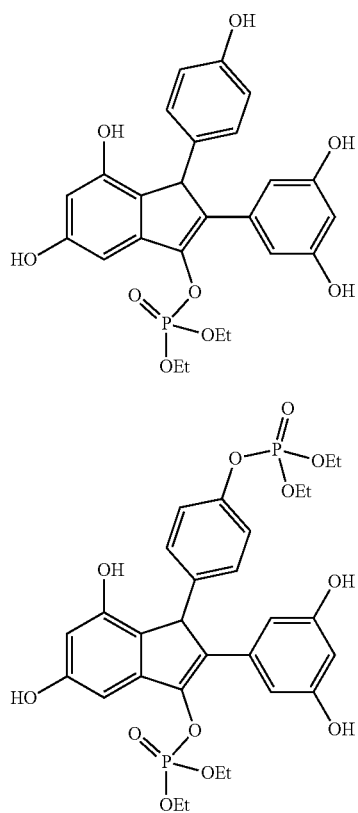

100 mg of compound 7a or 7b was weighed, dissolved in 20 mL of anhydrous dichloromethane, a solution of a 10- to 15-fold equivalent of boron tribromide in dichloromethane (1 mol/L) was added under ice bath, and then transferred to room temperature to react for 8 hours until the reaction was completed as detected by TLC. Separation and purification were performed through a reversed-phase chromatography column to obtain the corresponding demethylation-protected target compounds 1a and 1b with yields of 48.0% and 54.0%, respectively. 1a: $^1$H-NMR (400 MHz, DMSO-d6) ppm: 9.30 (1H, s), 9.15 (3H, s), 8.99 (1H, s), 6.81 (2H, d, J=8.0 Hz), 6.48 (2H, d, J=8.0 Hz), 6.47 (1H, d, J=2.0 Hz), 6.36 (2H, d, J=2.0 Hz), 6.06 (1H, d, J=2.0 Hz), 6.05 (1H, t, J=2.0 Hz), 4.84 (1H, s), 4.11-3.93 (8H, m), 1.25-1.01 (12H, m). ESI-MS m/z: 637.15 [M+H]$^+$; $C_{29}H_{34}O_{12}P_2$: HRMS calcd. 637.1596 [M+H]$^+$, Found: 637.1622 [M+H]$^+$. 1b: $^1$H-NMR (400 MHz, DMSO-d$_6$) δ ppm: 9.19 (1H, s), 9.08 (2H, s), 9.02 (1H, s), 8.97 (1H, s), 6.78 (2H, d, J=8.0 Hz), 6.46 (2H, d, J=8.0 Hz), 6.45 (1H, d, J=2.0 Hz), 6.33 (1H, d, J=2.0 Hz), 6.04 (1H, d, J=2.0 Hz), 6.02 (1H, d, J=2.0 Hz), 4.67 (1H, d), 4.13-3.91 (4H, m), 1.21 (3H, t), 1.11 (3H, t). ESI-MS m/z: 501.12 [M+H]$^+$; $C_{25}H_{25}O_9P$: HRMS calcd. 501.1309 [M+H]$^+$, Found: 501.1330 [M+H]$^+$.

Example 8: Lipid-Water Partition Coefficient Determination and Stability Test for Isopaucifloral F-PP (1a) and Isopaucifloral F-P (1b)

① Determination of lipid-water partition coefficients: a standard curve was first made. Target compounds 1a and 1b were weighed at a certain amount and prepared into a solution with chromatographic grade acetonitrile, respectively. Their respective solution was subjected to the HPLC sample injection analysis. HPLC conditions were: mobile phase: 5%~95% acetonitrile/water, gradient elution, a flow rate of 0.6 mL/min, a sample injection volume of 10 μL, a detection wavelength of 254/280 nm, run for 20 min. The retention time and peak area were recorded, and the standard curve was obtained by regressing the concentration and the peak area.

Moreover, 10 mL of water and 10 mL of n-octanol were taken into a 25 mL eggplant-shaped flask and stirred for 24 hours until the two phases were saturated with each other. The mixed solution was then transferred to a separatory funnel. Let it stand for liquid separation. 1 mL of the upper layer (saturated n-octanol layer) was taken, about 2 mg of the compound to be tested was added to vortex for 5 minutes to fully dissolve, and 1 mL of saturated aqueous phase was additionally taken and mixed with the saturated n-butanol phase in which the compound was dissolved. After vortexing for 5 minutes and oscillation for 24 hours in a water bath at 37° C., centrifugation was performed at 3500 rpm for 15 minutes. The upper n-octanol layer and the lower aqueous layer were respectively taken for the sample injection analysis under HPLC conditions. The HPLC conditions were the same as when the standard curve was made. The peak areas of the upper n-octanol layer and lower aqueous layer were recorded and substituted into the standard curve to obtain the concentrations of the compound. The concentration measured for the upper layer is the drug concentration Co in the oil phase (n-octanol phase) and the concentration measured for the lower layer is the drug concentration Cw in the aqueous phase. The calculation method of the oil-water partition coefficient log P is as follows: log P=log Co/Cw.

The log P of isopaucifloral F-PP (1a) is 2.60; and the log P of the compound isopaucifloral F-P (1b) is 2.25. Both compounds have a log P of between 1 and 3 and have certain druggability. Compared with isopaucifloral F (with a log P of 1.34), the target compounds have larger log P values and significantly improved lipid solubility.

② Determination of plasma stability: the DMSO stock solutions of the target compounds were dissolved at an appropriate amount in 4 mL of plasma to reach a concentration of 200 μg/mL and contain no more than 0.1% of DMSO, and incubated in a water bath at 37° C. 200 μL was taken at 0, 5, 15, 30 minutes and 1, 2, 4, 6, 10, 24, and 48 hours, and a 3-fold volume of chromatographic grade acetonitrile was added to precipitate the protein. It was subjected to vortexing and oscillation for 5 minutes. After centrifugation, 200 μL of the supernatant was taken for the HPLC sample injection analysis, and the liquid phase conditions were the same as previously described.

After incubation for 48 hours in plasma, the concentration of parent drug of the compound isopaucifloral F-PP (1a) accounted for 94.17% of the initial concentration; and the concentration of parent drug of the compound isopaucifloral F-P (1b) accounted for 93.74% of the initial concentration, which can show that the target compounds have better stability in plasma.

③ Determination of cell fluid stability: in the intracellular stability experiment, about 2 million MC3T3-E1 Subclone 14 cells in logarithmic growth phase were digested and collected in a 1 mL centrifuge tube, 200 μL of cell lysate was added to lyse the cells, and 800 μL of a PBS solution was then added to reach a total volume of 1 mL. Similarly, it was incubated in a water bath at 37° C., 100 μL was taken at 0, 5, 15, 30, 45, and 60 minutes, and a 3-fold volume of chromatographic grade acetonitrile was added to precipitate the protein. It was subjected to vortexing and oscillation for 5 minutes. After centrifugation, 200 μL of the supernatant was taken for the HPLC sample injection analysis, and the liquid phase conditions were the same as previously described.

The target compounds isopaucifloral F-PP (1a) and isopaucifloral F-P (1b) did not substantially dissociate within 60 minutes in the cell lysate system. It can be judged that the compounds should exist in the form of original drugs, and have no hydrolysis of diethyl phosphate groups.

Through the investigation of the stability of both target compounds, it was found that they are stable in plasma, do not dissociate in cells, and exist in the form of original drugs. The compounds have a log P of between 1 and 3, the Log P of the compound isopaucifloral F-PP (1a) is 2.60; the Log P of the compound isopaucifloral F-P (1b) is 2.25, and they have certain druggability.

150 μL of DMSO was added to each well to completely dissolve the purple crystal formazan formed by live cells and MTT. The optical density (OD) value was measured at 490 nm with a microplate reader. The proliferation rate was calculated according to the following formula:

Proliferation rate=[(the average OD value of the administration group−the average OD value of the blank group)/(the average OD value of the culture fluid control group−the average OD value of the blank group)].

The results showed that isopaucifloral F-PP (1a), isopaucifloral F-P (1b) and isopaucifloral F have significantly higher promoting effects on the proliferation of MC3T3-E1 Subclone 14 than the positive control drug genistein. The proliferation rates are 114%, 148%, and 124%, respectively.

TABLE 1

Proliferative Activity of Target Compounds on MC3T3-E1 Subclone 14

| | Proliferation Rate | | | | |
| --- | --- | --- | --- | --- | --- |
| Group | Isopaucifloral F-PP (1a) | Isopaucifloral F-P (1b) | Isopaucifloral F | GEN | E2 |
| $10^{-4}$ M | 0.67 ± 0.029 | 1.48 ± 0.077 | 1.24 ± 0.028 | 0.02 ± 0.0003 | 0.05 ± 0.002 |
| $10^{-5}$ M | 1.14 ± 0.032 | 1.07 ± 0.034 | 1.06 ± 0.014 | 0.71 ± 0.007 | 0.82 ± 0.003 |
| $10^{-6}$ M | 1.06 ± 0.031 | 1.04 ± 0.013 | 1.02 ± 0.024 | 1.05 ± 0.019 | 1.07 ± 0.019 |
| $10^{-7}$ M | 1.06 ± 0.031 | 1.01 ± 0.006 | 0.98 ± 0.020 | 0.99 ± 0.003 | 1.08 ± 0.003 |
| $10^{-8}$ M | 1.01 ± 0.030 | 1.00 ± 0.040 | 0.98 ± 0.045 | 1.01 ± 0.005 | 1.07 ± 0.005 |
| $10^{-9}$ M | 0.99 ± 0.030 | 1.01 ± 0.003 | 0.95 ± 0.016 | 1.03 ± 0.003 | 1.06 ± 0.003 |

Example 9: Study on In Vitro Osteogenesis Promoting Abilities of Isopaucifloral F-PP (1a) and Isopaucifloral F-P (1b)

① Proliferation-promoting effect of the compounds on mouse osteoblast precursor cells MC3T3-E1 Subclone 14 (see Table 1): the proliferation-promoting effect of target compounds 1a and 1b on MC3T3-E1 Subclone 14 was determined by MTT assay. Genistein and estradiol were used as positive control groups. MC3T3-E1 Subclone 14 was cultured using the α-MEM medium containing 10% FBS in a constant temperature incubator at 37° C. with 5% $CO_2$. The MC3T3-E1 Subclone 14 cells in logarithmic growth phase and in good condition were digested with addition of an appropriate amount of trypsin (commercially available from GIBCO), and the cells were collected. The cells were resuspended in the α-MEM medium containing 10% FBS, and seeded on a 96-well plate at an amount of 2000 cells per well. After cell adhesion, the medium was changed to the α-MEM medium containing 10% FBS of different concentrations of compounds at 200 μL per well. The cells with the culture fluid containing 0.2% DMSO added thereto were used as a negative control group of the medium. The medium was added to the wells without seeded cells as a blank control group. Six replicate wells were set for each concentration. The medium was changed once every 2 days, and on the $6^{th}$ day of administration, a 20 μL MTT/PBS solution at 5 mg/mL was added to the above 96-well plate, and the incubation was continued for 4 hours. After the time point, the liquid was carefully aspirated and ② Study on the differentiation-promoting effect of compounds on mouse osteoblast precursor cells MC3T3-E1 Subclone 14 (see Table 2): MC3T3-E1 subclone 14 cells were digested with pancreatin and collected and then seeded into a 6-well plate at $4 \times 10^4$/well. After 12 h adhesion, the medium was changed to a differentiation medium containing different concentrations of 1a, 1b, isopaucifloral F and the positive control drug genistein GEN. The administration concentrations of the compounds were $10^{-4} \sim 10^{-9}$ M, respectively; and the administration concentration of the positive control drug group genistein GEN was $10^{-6}$ M, a concentration at which it had the highest osteogenesis promoting ability as reported in the literature. On the $6^{th}$ day of administration, each well was washed twice with PBS, 150 uL of Western and IP cell lysate (with no protein inhibitor, commercially available from Beyotime) was then added to lyse the cells. This operation was performed on ice. 50 uL of cell lysate was diluted to 250 uL with PBS. 50 uL of dilution was additionally transferred to a 96-well plate for an ALP enzyme activity assay. The absorbance of each well in the 96-well plate was measured with a microplate reader at 405 nm.

The results showed that the ALP enzyme activities of isopaucifloral F-PP (1a), and isopaucifloral F-P (1b), and isopaucifloral F are all higher than those of the control group, i.e., 2.36 times (with enzyme activity increased by 136%), 1.20 times (with enzyme activity increased by 19.5%), and 1.14 times (with enzyme activity increased by 13.5%) those of the control group, respectively.

TABLE 2

Relative Values of ALP Enzyme Activity in Each Experimental Group

| Group | ALP enzyme activity relative values (experimental group/blank group) | | | | |
| --- | --- | --- | --- | --- | --- |
| | 7a | 7b | Isopaucifloral F | GEN | E2 |
| $10^{-4}$ M | 2.362 ± 0.04 | 0.919 ± 0.04 | 0.732 ± 0.03 | / | / |
| $10^{-5}$ M | 1.440 ± 0.31 | 0.986 ± 0.17 | 0.951 ± 0.04 | / | / |
| $10^{-6}$ M | 1.023 ± 0.05 | 0.993 ± 0.01 | 0.954 ± 0.02 | 1.341 ± 0.01 | / |
| $10^{-7}$ M | 0.877 ± 0.01 | 1.195 ± 0.02 | 1.135 ± 0.06 | / | / |
| $10^{-8}$ M | 0.860 ± 0.01 | 1.097 ± 0.07 | 1.029 ± 0.11 | / | 1.050 ± 0.02 |
| $10^{-9}$ M | 0.861 ± 0.05 | 0.899 ± 0.11 | 0.864 ± 0.05 | / | / |

③ Study on the effect of target compounds on the formation of calcium nodules in osteoblasts (see FIG. 1 and Table 3 for details): after being digested, the cells were seeded into a 6-well plate at $4\times10^4$/well. After 12 h adhesion, the medium was changed to a differentiation medium containing different concentrations of 1a, 1b, isopaucifloral F and positive control drug genistein GEN. The administration concentrations of the compounds were $10^{-4}$~$10^{-9}$ M, respectively; and the concentration of genistein is $10^{-6}$ M. On the 15$^{th}$ day of administration, the medium was aspirated, each well was then washed twice with PBS, the cells were then fixed with 95% ethanol for 10 minutes and rinsed twice with double distilled water. 2 mL of a 0.1% Alizarin Red-Tris. HCl solution (PH=8.3) was added to each well, the cells were incubated at 37° C. for 30 minutes, then rinsed with double distilled water for several times, dried, and mounted. The formation of calcium nodules was further observed by taking pictures under a 40× microscope. Afterwards, 1 mL of a 10% cetylpyridinium chloride solution was added to each well, and the incubation was carried out for 30 minutes to release the Alizarin Red staining. The solution was transferred to a 96-well plate at 200 uL per well, the absorbance was measured at 562 nm using a microplate reader, and a quantitative analysis of calcium nodules was performed.

Compared with the control group, both the target compounds can promote the formation of calcium nodules. Isopaucifloral F-PP (1a) at $10^{-7}$ M results in the greatest amount of formed calcium nodules with a relative value of 1.446. Isopaucifloral F-P (1b) at $10^{-6}$ M results in the largest amount of formed calcium nodules with a relative value of 1.182.

Figure 2:
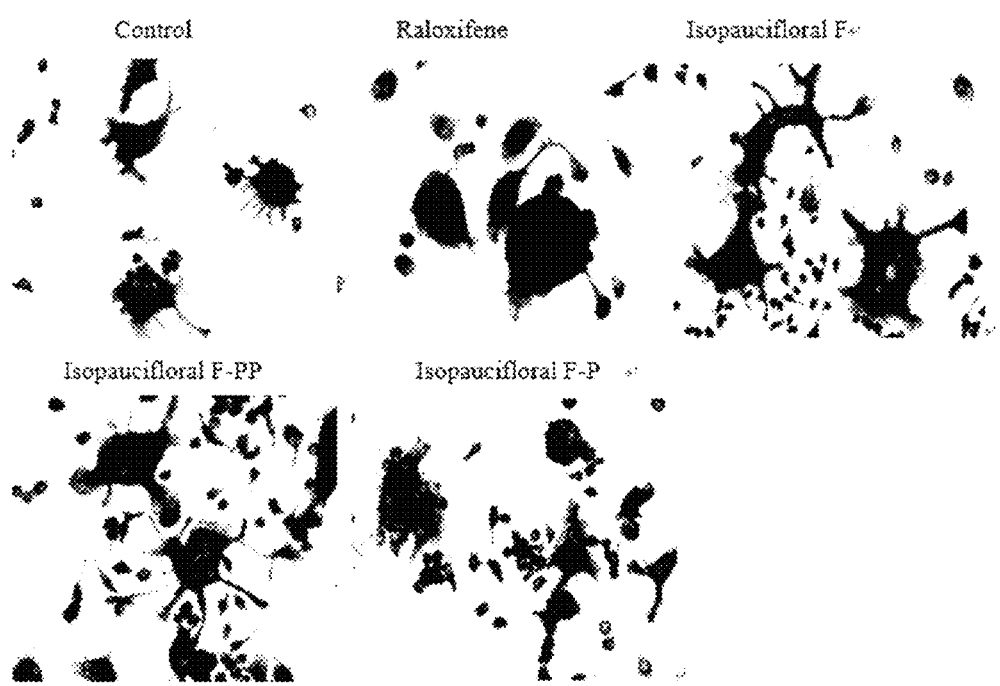
FIG. 2 shows the status of TRAP-positive multinucleated osteoclasts in each experimental group (×200).

Example 10: Study on Efficacy of Isopaucifloral F-PP (1a) and Isopaucifloral F-P (1b) in Bone Resorption Inhibition The above mouse mononuclear macrophages RAW264.7 were seeded in a 96-well plate, and after they adhered, the medium was changed into 1a and 1b at concentrations of $10^{-4}$ M, $10^{-6}$ M, and $10^{-8}$ M. The induction medium of the lead compound isopaucifloral F group and the positive control drug Raloxifene used the non-administration group as the negative control group (Control group). After being cultured for 5 days, the cells were stained with a tartrate-resistant acid phosphatase TRAP incubation solution, mounted with glycerol gelatin, and observed under light microscope to count stained TRAP-positive multinucleated cells (as shown in FIG. 2). The inhibition rate of the administered drug on the number of TRAP-positive multinucleated cells is $$(n_{TRAP\text{-}positive\ multinucleated\ osteoclasts\ in\ the\ negative\ control\ group} - n_{TRAP\text{-}positive\ multinucleated\ osteoclasts\ in\ the\ drug\ administration\ group})/n_{TRAP\text{-}positive\ multinucleated\ osteoclasts\ in\ the\ negative\ control\ group} \times 100\%.$$

The results showed (as shown in Table 4) that the phosphate compounds isopaucifloral F-PP (1a) and isopaucifloral F-P (1b) have better osteoclast formation inhibiting abilities than Raloxifene, and the introduction of phosphate groups has greatly improved their osteoclast formation inhibiting abilities. Their inhibitory activities on osteoclasts are comparable, being 62.4% and 65%, respectively, and are significantly higher than that of isopaucifloral F, being 2.2 and 2.3 times that of isopaucifloral F, respectively.

TABLE 3

Relative Values of the Number of Calcium Nodules in Each Experimental Group (Control = 1)

| Group | Relative values of calcium nodule amount (experimental group/blank group) | | | | |
| --- | --- | --- | --- | --- | --- |
| | 1a | 1b | Isopaucifloral F | Genistein | E2 |
| $10^{-4}$ M | 1.08 ± 0.05 | 1.123 ± 0.05 | 0.982 ± 0.04 | / | / |
| $10^{-5}$ M | 1.261 ± 0.06 | 1.096 ± 0.02 | 0.915 ± 0.03 | / | / |
| $10^{-6}$ M | 1.352 ± 0.05 | 1.182 ± 0.04 | 0.932 ± 0.03 | 1.028 ± 0.03 | / |
| $10^{-7}$ M | 1.446 ± 0.05 | 1.16 ± 0.04 | 0.964 ± 0.03 | / | / |
| $10^{-8}$ M | 1.301 ± 0.05 | 1.16 ± 0.03 | 0.917 ± 0.03 | / | 1.007 ± 0.02 |
| $10^{-9}$ M | 1.26 ± 0.04 | 1.139 ± 0.03 | 0.916 ± 0.03 | / | / |

TABLE 4

Inhibition Rates of Osteoclasts in Each Experimental Group
(Number of Osteoclasts in the Control Group being 117)

| Group | $10^{-4}$ M | | $10^{-6}$ M | | $10^{-8}$ M | |
|---|---|---|---|---|---|---|
| | Number of Osteoclasts (cell) | Relative Inhibition Rates (%) | Number of Osteoclasts (cell) | Relative Inhibition Rates (%) | Number of Osteoclasts (cell) | Relative Inhibition Rates (%) |
| Isopaucifloral F-PP (1a) | 44 | 62.4 | 67 | 42.7 | 72 | 38.5 |
| Isopaucifloral F-P (1b) | 41 | 65 | 69 | 41 | 77 | 34.2 |
| Isopaucifloral F | 84 | 28.2 | 85 | 27.4 | 102 | 12.8 |
| Raloxifene | / | / | 64 | 45.3 | 67 | 42.7 |

Note:
the number of osteoclasts in the control group was 117; 8 replicate wells were made for each group.

Example 11: Study on Metabolic Stabilities of Isopaucifloral F-PP (1a) and Isopaucifloral F in Human Liver Microsomes Experimental method: the incubation system comprising human liver microsomes, cofactors, and PBS was pre-incubated at 37° C. for 3 minutes, and a substrate was added to start the reaction. Sampling was performed at 0, 1, 5, 10, 15, 20, 30, and 60 minutes after the start of the reaction, and an appropriate terminator was added to terminate the reaction. Sample treatment (n=3): appropriate internal standards were added to each; after vortexing, centrifugation was performed at a high speed, the supernatant was taken, and the substrate was detected by employing HPLC-MS/MS. The peak area at a time point 0 min was taken as 100%. Peak areas at other time points were converted to the remaining percentage, the natural logarithm of the remaining percentage at each time point versus incubation time was plotted, and a slope (−k) was calculated by linear regression, and then $CL_{int}$ (mL·min$^{-1}$·mg$^{-1}$) was calculated based on the inherent clearance $(CL_{int})$=(k×the volume of incubation solution)/mass of liver microsomes. $T_{1/2}$ was calculated by Graphpad Prism 5 software (as shown in Table 5).

TABLE 5

Metabolic Stability Data of Isopaucifloral F-PP (1a)
and Isopaucifloral F in Human Liver Microsomes

| Group | $T_{1/2}$ (min) | $CL_{int(liver)}$ (mL/min/kg) |
|---|---|---|
| R-1a | 32.5 | 38.4 |
| S-1a | 145 | 8.6 |
| Isopaucifloral F | 10.1 | 123.4 |

The results of the in vitro metabolism in human liver microsomes (see Table 5) showed that (1) R-1a and S-1a have better metabolic stabilities than isopaucifloral F, and clearance rates $CL_{int(liver)}$ thereof are 38.4 and 8.6 mL/min/kg, respectively; isopaucifloral F is metabolized the fastest with a clearance rate of 123.4 mL/min/kg. (2) The metabolic stabilities of S-1a and R-1a are 3.3 times and 14.5 times that of isopaucifloral F, respectively. (3) The metabolic stability of S-1a is 4.5 times that of R-1a. From the above results, it can be seen that S-1a is more suitable for research and development as a candidate drug.

Example 12: Study on In Vivo Pharmacokinetics of Isopaucifloral F-PP (1a) in Rats S-1a was selected for the study on in vivo pharmacokinetics in SD rats; the intravenous dose and the oral dose were 5 mg/kg and 20 mg/kg, respectively; blood samples were collected from the orbit at each time point of 5 min, 8 min, 15 min, 30 min, 1 h, 2 h, 3 h, 4 h, 6 h, 8 h, 10 h, 24 h, and after centrifugation, the concentration of the drug in the plasma at each time point was determined by LC-MS/MS, and the in vivo preliminary pharmacokinetic parameters were estimated using a non-compartmental model method with the DAS software (version 2.0). The experimental results were as follows:

TABLE 6

Data of In Vivo Pharmacokinetics (PK) of
Optically Pure Isomer S-1a in SD Rats

| Parameters | Unit | Compound S-1a | | F |
|---|---|---|---|---|
| | | iv (5 mg/kg) | po (20 mg/kg) | |
| $AUC_{0-t}$ | μg/L*h | 14307 | 26455 | 41.9% |
| $AUC_{0-\infty}$ | μg/L*h | 15881 | 26632 | |
| $MRT_{0-\infty}$ | h | 9.69 | 2.31 | |
| $t_{1/2}$ | h | 10.89 | 5.72 | |
| Tmax | h | 0.083 | 1 | |
| Vz | L/kg | 24.74 | 31.00 | |
| CLz | L/h/kg | 1.57 | 3.75 | |

The results from Table 6 showed that (1) S-1a has an oral bioavailability of 41.9% and is suitable for research and development as an oral drug (>30%).

Example 13: Study on Acute Toxicity of Isopaucifloral F-PP (1a) and Isopaucifloral F To further investigate the toxicity of the preferred compounds, we preferably selected isopaucifloral F-PP (1a) and its precursor isopaucifloral F for in vivo acute toxicity experiments in mice. Healthy adult Kunming mice weighing 20±2 g were divided into 5 groups at random with 10 mice per group, half female and half male. A single dose was administered via intraperitoneal injection at an administration volume of 0.2 mL/10 g. The behavior status and death of the mice were continuously observed and recorded for 14 days. The experimental data were calculated by SPSS software (IBM SPSS Statistics 19) using the Bliss method, and the results showed that the acute toxicity LD50 of both compounds is >150 mg/kg, and the therapeutic index TI is >toxic dose (150 mg)/effective dose (10 μg)=15000, indicating that both compounds have good safety.

Figure 3:
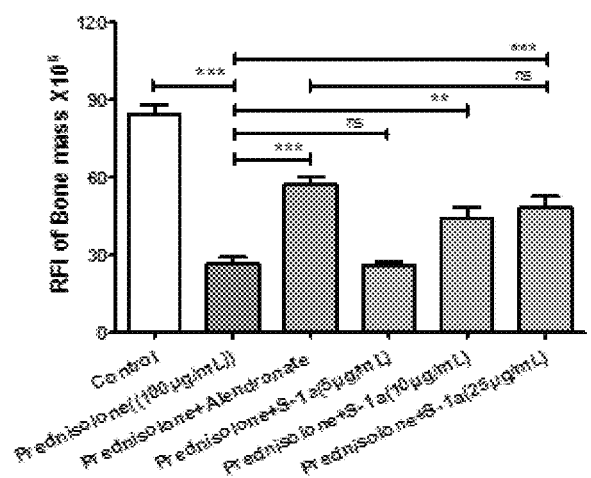
FIG. 3 shows the study on the S-1a zebrafish osteoporosis model (with Control as a blank control group, Prednisolone as a model group, and Alendronate as a positive drug control group; ns, not significant; *P<0.0001, P<0.001).

Example 14: Study on Pharmacodynamics of Isopaucifloral F-PP (1a) on the Zebrafish Osteoporosis Model On the basis of good pharmacokinetics and good safety, S-1a and the clinical first-line drug Alendronate sodium were selected for administration, the zebrafish model larvae were cultured to 10 days after fertilization (10 dpf), and then sacrificed by anesthesia. After fixation with 4% paraformaldehyde, the fish juveniles were bleached with a 30% $H_2O_2$-containing bleach prepared with 1% KOH until the eye pigment was removed; the head bones of zebrafish juveniles were then stained with Alizarin Red; the fish juveniles were then made transparent using a mixed solution of 1% KOH and glycerol with a gradient ratio of 3:1, respectively; and finally, the fish juveniles were stored in pure glycerol. The head ventral photos of fish juveniles were taken using a microscope, and an image analysis software Image-Pro Plus 6.0 was then used to analyze and calculate the staining area and cumulative optical density of the head bones of the fish juveniles to reflect the amount of bone mineralization (as shown in FIG. 3). The results showed that (1) S-1a can recover zebrafish from osteoporosis in a concentration-dependent manner (5 μg/mL, 10 μg/mL, 25 μg/mL); (2) S-1a has a concentration of 25 μg/mL which can recover zebrafish from osteoporosis, and is comparable to the control drug Alendronate sodium (100 μg/mL) in efficacy, and S-1a can be considered as a clinical candidate drug.

The invention claimed is:

1. An isopaucifloral F phosphate compound of the following formula (1) and pharmaceutically acceptable salts thereof:

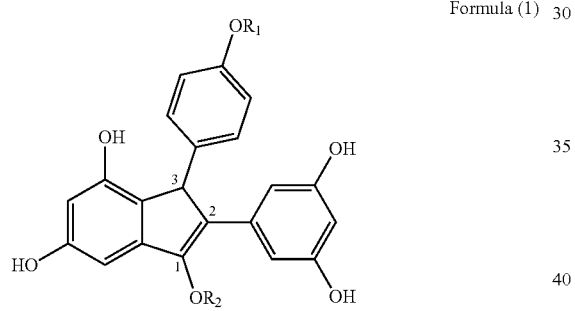

Formula (1)

wherein $R_1$ is independently a phosphate group or a hydrogen atom; and $R_2$ is independently a phosphate group, wherein the phosphate group is

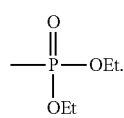

2. The isopaucifloral F phosphate compound and pharmaceutically acceptable salts thereof as recited in claim 1, characterized in that said $R_1$=H, and $R_2$ is a phosphate group, wherein the phosphate group is

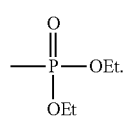

3. The isopaucifloral F phosphate compound and pharmaceutically acceptable salts thereof as recited in claim 1, characterized in that said $R_1$=$R_2$, and is a phosphate group, wherein the phosphate group is

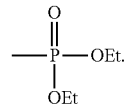

4. The isopaucifloral F phosphate compound and pharmaceutically acceptable salts thereof as recited in claim 1, characterized in that said compound is of the structure selected from:

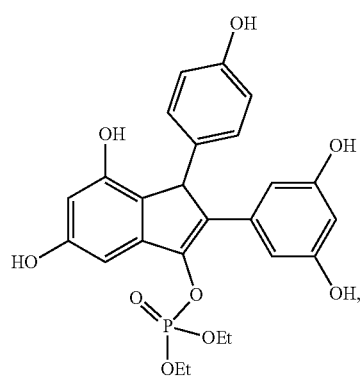

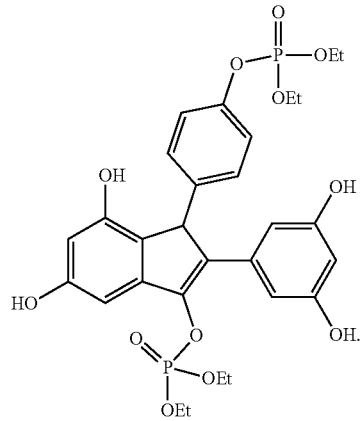

5. The isopaucifloral F phosphate compound and pharmaceutically acceptable salts thereof as recited in claim 1, characterized in that they are racemic mixtures.

6. The isopaucifloral F phosphate compound and pharmaceutically acceptable salts thereof as recited in claim 1, characterized in that they are optically pure isomers with a C3-position configuration being an R or S configuration.

7. A method of treating osteoporosis comprising administering an effective amount of an isopaucifloral F phosphate compound or pharmaceutically acceptable salts thereof of claim 1.

8. A pharmaceutical composition for treating osteoporosis, comprising the isopaucifloral F phosphate compound and pharmaceutically acceptable salts thereof as recited in claim 1, and pharmaceutically acceptable excipients.

* * * * *